United States Patent [19]

Atwal

[11] Patent Number: 5,612,370
[45] Date of Patent: Mar. 18, 1997

[54] PHENYLGLYCINE AND PHENYLALANINEN AMIDO BENZOPYRAN DERIVATIVES

[75] Inventor: Karnail S. Atwal, Newtown, Pa.

[73] Assignee: Bristol-Myers Squibb Company, Princeton, N.J.

[21] Appl. No.: 484,765

[22] Filed: Jun. 7, 1995

[51] Int. Cl.⁶ .......................... A61K 31/35; C07D 311/68
[52] U.S. Cl. .......................... 514/456; 549/404; 549/399; 549/345; 549/220; 548/525; 548/413; 548/343.5; 548/266.4; 548/256; 548/253; 548/240; 548/215; 546/196; 514/397; 514/383; 514/382; 514/374; 514/320; 514/100
[58] Field of Search .......................... 514/456, 397, 514/383, 382, 374, 320, 100; 549/404, 399, 345, 220; 548/525, 413, 343.5, 266.4, 256, 253, 240, 215; 546/196

[56] References Cited

U.S. PATENT DOCUMENTS

| | | |
|---|---|---|
| 3,330,838 | 7/1967 | Augstein et al. . |
| 3,812,157 | 5/1974 | Lin et al. . |
| 3,953,506 | 4/1976 | Spicer et al. . |
| 4,238,501 | 12/1980 | Kabbe et al. . |
| 4,251,537 | 2/1981 | Evans . |
| 4,363,811 | 12/1982 | Evans et al. . |
| 4,366,163 | 12/1982 | Evans et al. . |
| 4,391,815 | 7/1983 | Evans . |
| 4,428,881 | 1/1984 | Hedrich et al. . |
| 4,481,213 | 11/1984 | Evans . |
| 4,568,692 | 2/1986 | Evans . |
| 4,571,406 | 2/1986 | Evans et al. . |
| 4,575,511 | 3/1986 | Evans et al. . |
| 4,602,022 | 7/1986 | Cozzi et al. . |
| 4,659,737 | 4/1987 | Kabbe et al. . |
| 4,687,779 | 8/1987 | Evans . |
| 4,734,421 | 3/1988 | Hammond et al. . |
| 4,772,603 | 9/1988 | Evans . |
| 4,782,083 | 11/1988 | Cassidy et al. . |
| 4,831,050 | 5/1989 | Cassidy et al. . |
| 4,904,784 | 2/1990 | Evans et al. . |
| 4,925,839 | 5/1990 | Quagliato et al. . |
| 4,943,582 | 7/1990 | Evans et al. . |
| 4,971,982 | 11/1990 | Attwood et al. . |
| 4,988,723 | 1/1991 | Shiokawa et al. . |
| 5,006,523 | 4/1991 | Atwal . |
| 5,011,837 | 4/1991 | Atwal et al. . |
| 5,013,853 | 5/1991 | Gericke et al. . |
| 5,021,432 | 6/1991 | Yamanaka et al. . |
| 5,028,711 | 7/1991 | Stenzel et al. . |
| 5,053,427 | 10/1991 | Stemp et al. . |
| 5,061,813 | 10/1991 | Atwal . |
| 5,071,871 | 12/1991 | Blarer et al. . |
| 5,082,858 | 1/1992 | Garcia et al. . |
| 5,095,016 | 3/1992 | Ohtuka et al. . |
| 5,096,914 | 3/1992 | Stenzel et al. . |
| 5,104,890 | 4/1992 | Shiokawa et al. . |
| 5,140,031 | 8/1992 | Atwal et al. . |
| 5,143,924 | 9/1992 | Gericke et al. . |
| 5,143,936 | 9/1992 | Yamanaka et al. . |
| 5,145,985 | 9/1992 | Timar et al. . |
| 5,210,234 | 5/1993 | Evans et al. . |
| 5,238,937 | 8/1993 | Gericke et al. . |
| 5,254,555 | 10/1993 | Stemp et al. . |
| 5,268,386 | 12/1993 | Harada et al. . |
| 5,276,168 | 1/1994 | Atwal . |
| 5,278,169 | 1/1994 | Atwal . |
| 5,286,753 | 2/1994 | Schaus et al. . |
| 5,310,750 | 5/1994 | Berge et al. . |
| 5,310,932 | 5/1994 | Atwal et al. . |
| 5,317,029 | 5/1994 | Inazu et al. . |
| 5,318,969 | 6/1994 | Yamanaka et al. . |
| 5,374,643 | 12/1994 | Atwal et al. . |
| 5,393,771 | 2/1995 | Atwal . |
| 5,401,848 | 3/1995 | Atwal . |

FOREIGN PATENT DOCUMENTS

| | | |
|---|---|---|
| 0076075 | 4/1983 | European Pat. Off. . |
| 0091748 | 10/1983 | European Pat. Off. . |
| 0093535 | 11/1983 | European Pat. Off. . |
| 0120427 | 10/1984 | European Pat. Off. . |
| 0126311 | 11/1984 | European Pat. Off. . |
| 0139992 | 5/1985 | European Pat. Off. . |
| 0205292 | 12/1986 | European Pat. Off. . |
| 0214818 | 3/1987 | European Pat. Off. . |
| 0247266 | 12/1987 | European Pat. Off. . |
| 0250077 | 12/1987 | European Pat. Off. . |
| 0274821 | 7/1988 | European Pat. Off. . |
| 0287196 | 10/1988 | European Pat. Off. . |
| 0339562 | 11/1989 | European Pat. Off. . |
| 0344747 | 12/1989 | European Pat. Off. . |
| 0350805 | 1/1990 | European Pat. Off. . |
| 0351767 | 1/1990 | European Pat. Off. . |
| 0359537 | 3/1990 | European Pat. Off. . |

(List continued on next page.)

OTHER PUBLICATIONS

A.P. Terent'ev et al., "Optically Active Isocyanates. III. Synthesis and Spectropolarimetric Study of Optically Active N–derivative of Urea", *Chemical Abstracts*, vol. 71, Abstract No. 69992h, p. 250 (1969).

(List continued on next page.)

*Primary Examiner*—Nicky Chan
*Attorney, Agent, or Firm*—Ellen K. Park

[57] ABSTRACT

Compounds having the formula

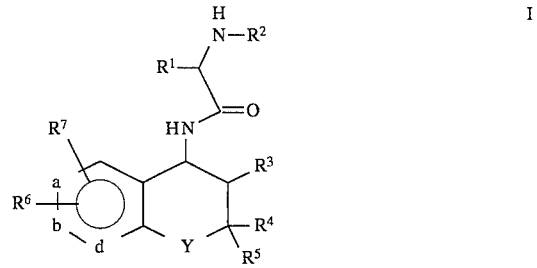

and pharmaceutically acceptable salts thereof wherein a, b and d are all carbon atoms or one of a, b and d is a nitrogen atom or —N(O)— and the others are carbon atoms; Y is a single bond, —$CH_2$—, —C(O)—, —O—, —S— or —N($R^8$)—; and $R^1$ to $R^7$ are as defined herein. These compounds have potassium channel activating activity and are useful, therefore for example, as cardiovascular agents.

5 Claims, No Drawings

FOREIGN PATENT DOCUMENTS

| | | |
|---|---|---|
| 0377966 | 7/1990 | European Pat. Off. . |
| 0377967 | 7/1990 | European Pat. Off. . |
| 0385584 | 9/1990 | European Pat. Off. . |
| 0389861 | 10/1990 | European Pat. Off. . |
| 0401010 | 12/1990 | European Pat. Off. . |
| 0402716 | 12/1990 | European Pat. Off. . |
| 0407200 | 1/1991 | European Pat. Off. . |
| 0412531 | 2/1991 | European Pat. Off. . |
| 0431741 | 6/1991 | European Pat. Off. . |
| 0462761 | 12/1991 | European Pat. Off. . |
| 0488616 | 6/1992 | European Pat. Off. . |
| 0501797 | 9/1992 | European Pat. Off. . |
| 0525768 | 2/1993 | European Pat. Off. . |
| 2801187 | 7/1978 | Germany . |
| 2204868 | 11/1988 | United Kingdom . |
| WO8707607 | 12/1987 | WIPO . |
| WO89/09217 | 10/1989 | WIPO . |
| WO91/09031 | 6/1991 | WIPO . |
| WO92/05174 | 4/1992 | WIPO . |
| WO92/14733 | 9/1992 | WIPO . |
| WO92/22293 | 12/1992 | WIPO . |

OTHER PUBLICATIONS

J. Bermudez et al., "5–Hydroxytryptamine (5–HT$_3$) Receptor Antagonists. 2. 1–Indolinecarboxamides", *J. Med. Chem.*, vol. 33, pp. 1929–1932 (1990).

P.D. Leeson et al., "4–Amido–2–carboxytetrahydroquinolines, Structure–activity Relationships for Antagonism at the Glycine Site of the NMDA Receptor", *J. Med. Chem.*, vol. 35, pp. 1954–1968 (1992).

J.L. Hughes et al., "Cardiovascular Activity of Aromatic Guanidine Compounds", *J. Med. Chem.*, vol. 18. No. 11, pp. 1077–1088 (1975).

M. Mazza et al., "N–Acilindoline Ad Attivita Fitotossica", *Farmaco. Ed. Sci.*, vol. 31, No. 10, pp. 746–754 (1976).

T. Sekiya et al., "Benzene–condensed Cyclic Amine β–amino Carboxamides as Antichycardiacs and Vasodilators", *Chemical Abstracts*, vol. 113, p. 694 (1990).

R. Albrecht et al., "Chemotherapeutic Nitroheterocycles. XI (1). Indanylamides and Indanylesters of 5–nitrofurancarboxylic Acids and Analogous Compounds as Antimicrobial Agents", *Chimie Therapeutique*, vol. 7, No. 1, pp. 9–13 (1972).

H.J. Petersen et al., "Synthesis and Hypotensive Activity of N–Alkyl–N"–cyano–N'–pyridylguanidines", *J. of Med. Chem.*, vol. 21, No. 8, pp. 773–781 (1978).

V.A. Ashwood et al., "Synethsis and Antihypertensive Activity of 4–(Cyclic amido)–2H–1–benzopyrans", *J. Med. Chem.*, 29, pp. 2194–2201 (1986).

C.R. Rasmussen et al., "Improved Procedures for the Preparation of Cycloalkyl–, Arylalkyl–, and Arylthioureas", *Synthesis*, pp. 456–459 (1988).

V.V. Mozolis et al., "Preparation of N–Substituted Thiourea", *Russian Chem. Reviews*, 42(7), pp. 587–595 (1973).

J.M. Evans et al., "Synthesis and Antihypertensive Activity of Substituted trans–4–Amino–3,4–dihydro–2, 2–dimethyl–2H–1–benzopyran–3–ols", *J. Med. Chem.*, 26, pp. 1582–1589 (1983).

R.W. Lang et al., "Synthesis of Selectively Trifluoromethylated Pyridine Derivatives as Potential Antihypertensives", *Helvetica Chimica Acta*, vol. 72, pp. 596–601 (1988).

P. Sebok et al., "Selective synthesis of Analogues of the Natural Precocenes, Synthesis and Regioselective (–Alkylation of 6–Chloro–and 6–Tert–Butyl–7,8–Dihyedroxy–2, 2–Dimethyl–4–Chromanones", *Heterocycles*, 27, pp. 2595–2607 (1988).

P. Teixidor et al., "Improved Preparation of Precocene II, Unexpected Results in the Reduction of Alkoxy Substituted Acetophenones and 4–Chromanones with Sodium Borohydride", *Heterocycles*, 27, pp. 2459–2465 (1988).

A. Banerji et al., "Enolates of O–Hydroxyacetophenones: Novel Synthesis of 2,2–Dialkyl–4–Chromanones", *Tetrahedrom Letters*, No. 38, pp. 2685–2686 (1979).

G. Ariamala et al., "A Simple Route for the Synthesis of 4–Chlorochromanes and Chroman–4–one", *Tetrahedrom Letters*, 29, No. 28, pp. 3487–3488 (1988).

PHENYLGLYCINE AND PHENYLALANINEN AMIDO BENZOPYRAN DERIVATIVES

BRIEF DESCRIPTION OF THE INVENTION

The present invention is directed to compounds of the formula

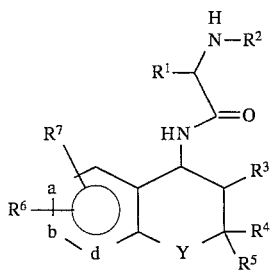

and pharmaceutically acceptable salts thereof. As used in formula I, and throughout the specification, the symbols have the following means:

a, b and d are all carbon atoms or one of a, b and d is a nitrogen atom or —N(O)— and the others are carbon atoms;

Y is a single hold, —CH$_2$—, —C(O)—, —O—, —S— or —N(R$^8$)—;

R$^1$ is a aryl, (aryl)alkyl, heterocyclo or (heterocyclo)alkyl;

R$^2$ is hydrogen, alkyl, —COR$^8$, —COOR$^8$, —CONR$^8$R$^9$ or —SO$_2$R$^8$;

R$^3$ is hydrogen, hydroxy or —OC(O)R$^8$;

R$^4$ and R$^5$ are each independently hydrogen, alkyl or arylalkyl; or R$^4$ and R$^5$ taken together with the carbon atom to which they are attached form a 5- to 7-membered carbocyclic ring;

R$^6$ is hydrogen, alkyl, haloalkyl, alkenyl, alkynyl, cycloalkyl, arylalkyl, (cycloalkyl)alkyl, —CN, —NO$_2$, —COR$^8$, —COOR$^8$, —CONHR$^8$, —CONR$^8$R$^9$, —CF$_3$, —S-alkyl,

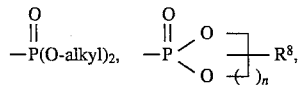

halogen, amino, substituted amino, —O-alkyl, —OCF$_3$, —OCH$_2$CF$_3$, —OCOalkyl, —OCONR$^8$alkyl, —NR$^8$COalkyl, —NR$^8$COOalkyl or —NR$^8$CONR$^9$, tetrazolyl, imidazole, oxazole or triazole, —SOR$^8$, —SO$_2$R$^8$ or —SO$_2$NR$^8$R$^9$;

R$^7$ is hydrogen, alkyl, halogen, hydroxy, —O-alkyl, amino, substituted amino, —NHCOR$^8$, —CN or —NO$_2$;

R$^8$ and R$^9$ are independently hydrogen, alkyl, haloalkyl, aryl, arylalkyl, cycloalkyl or (cycloalkyl)alkyl; or R$^8$ and R$^9$ taken together with the atoms to which they are attached form a 5- to 7-membered ring; and n is an integer of 1 to 3.

The compounds of this invention possess antiischemic activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group).

The term "alkyl" refers to both straight and branched chain groups having 1 to 8 carbon atoms preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups optionally substituted with one or more substituents selected from halogen, alkoxy, aryl, alkylaryl, haloaryl, cycloalkyl, (cycloalkyl)alkyl, hydroxy, alkylamino, alkyl-substituted amino, alkanoylamino, arylcarbonylamino, nitro, cyano, thiol or alkylthio.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups having at least 2 carbon atoms further containing at least one carbon to carbon double bond.

The term "alkynyl" refers to any of the above alkyl groups having at least 2 carbon atoms further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl or 2-naphthyl; or phenyl, 1-naphthyl or 2-naphthyl, mono-substituted with (C$_1$–C$_4$)-alkyl, (C$_1$–C$_4$)-alkylthio, (C$_1$–C$_4$)-alkoxy, halo, nitro, cyano, hydroxy, amino, (alkyl)amino, alkyl-substituted amino, —NH—(C$_1$–C$_4$)-alkyl, —N((C$_1$–C$_4$)-alkyl)$_2$, —CF$_3$, —OCHF$_2$,

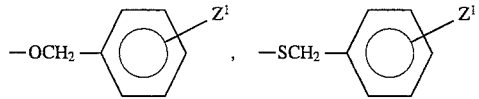

(where Z$^1$ is hydrogen, (C$_1$–C$_4$)-alkyl, (C$_1$–C$_4$)-alkylthio, (C$_1$–C$_4$)-alkoxy, halo, hydroxy or —CF$_3$), —O—CH$_2$-cycloalkyl, or —S—CH$_2$-cycloalkyl; or phenyl, 1-naphthyl or 2-naphthyl, di-substituted with methyl, methoxy, methylthio, halogen, —CF$_3$, nitro, amino, —OCHF$_2$, carboxylic acid or carboxylic ester. The term "aryl" also includes those groups listed above fused to a five- or six-membered ring which optionally contains an O, S or N atom (the nitrogen atom being substituted by an R$^7$ group). Preferred aryl groups include unsubstituted phenyl and monosubstituted phenyl wherein the substituents are (C$_1$–C$_4$)-alkyl, methoxy, halo, nitro, cyano or —CF$_3$.

The term "heterocyclo" or "hetero" refers to fully saturated or unsaturated rings of 5 to 7 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term "hetero" also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a $(C_1-C_4)$-alkyl, aryl, $(C_1-C_4)$-alkylthio, $(C_1-C_4)$-alkoxy, halo, nitro, keto, cyano, hydroxy, azo, thiazo, amino, —NH—$(C_1-C_4)$-alkyl, —N$((C_1-C_4)$-alkyl$)_2$, —$CF_3$, (aminoester)alkyl, carboxylic acid, carboxylic ester, —$OCHF_2$ or $(C_1-C_4)$-alkoxy further substituted with a carboxylic acid or such monocyclic and bicyclic rings wherein two or three available carbons have substituents selected from methyl, methoxy, methylthio, halo, —$CF_3$, nitro, hydroxy, amino and —$OCHF_2$.

The term "substituted amino" refers to a group of the formula —$NZ^2Z^3$ wherein $Z^2$ is hydrogen, alkyl, cycloalkyl, aryl, arylalkyl, (cycloalkyl)alkyl, morpholinylalkyl, heterocyclo or (heterocyclo)alkyl and $Z^3$ is hydrogen, alkyl, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when $Z^2$ is hydrogen, then $Z^3$ is other than hydrogen; or $Z^2$ and $Z^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl- 1-piperazinyl, 4-diarylalkyl- 1-piperazinyl, 1-pyrrolidinyl, 1-piperidinyl, or 1-azepinyl, optionally substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic adds, such as mineral adds, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $(C_1-C_4)$-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The above described processes can utilize racemates, enantiomers or diastereomers as starting materials. When diastereomeric products are prepared, they can be separated by conventional methods for example, chromatographic or fractional crystallization.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula I where $R^2$ is a tert-butoxycarbonyl group (BOC;—COO-tertBu) can be prepared by reacting a compound of formula

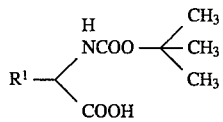

II with 1-hydroxybenzotriazole in the presence of dicyclohexylcarbodiimide to provide an activated ester which is then reacted with a compound of formula

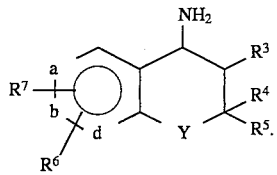

III

Compounds of formula I where $R^2$ is hydrogen can be prepared from compounds of formula I where $R^2$ is BOC by treatment with trifluoroacetic acid in an organic solvent such as dichloromethane.

Compounds of formula I where $R^2$ is —$COR^8$ can be prepared from compounds of formula I where $R^2$ is hydrogen by acylation with an acid chloride of formula

in the presence of an organic base such as pyridine or triethylamine.

Compounds of formula I where $R^2$ is —$COOR^8$ can be prepared by reacting a compound of formula I where $R^2$ is hydrogen, with a chloroformate of formula

in an organic solvent and an organic base such as pyridine and triethylamine.

Compounds of formula I where $R^2$ is —$CONHR^8$ can be prepared by treatment of a compound of formula I wherein $R^2$ is hydrogen, with an isocyanate of formula

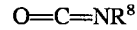

in the presence of an organic base such as pyridine or triethylamine.

Other compounds of formula I where $R^2$ is —$CONR^8R^9$ can be prepared from compounds of formula I wherein $R^2$ is hydrogen, by treatment with a compound of formula

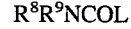

where L is a leaving group such as chlorine, phenol or 4-nitrophenol.

Compounds of formula I where $R^2$ is $-SO_2R^8$ can be prepared by treatment of a compound of formula I where $R^2$ is hydrogen, by treatment with a sulfonyl chloride of formula $$R^8SO_2Cl$$

in the presence of an organic base such as pyridine and triethylamine.

Compounds of formula I where $R^2$ is alkyl can be prepared from compounds of formula I wherein $R^2$ is hydrogen, by treatment with an alkyl halide of formula $$R^2-X$$

where X is chlorine, bromine or iodine, in the presence of a base such as triethylamine or potassium carbonate and an organic solvent.

Compounds of formula II are standard amino acids where the amine is protected as a tert-butoxycarbonyl group. Most of the compounds of formula II are commercially available or they can be prepared by standard methods described in the literature.

The amino alcohol of formula III wherein $R^3$ is trans-hydroxy can be prepared by methods described in the literature, such as by J. M. Evans et al., *J. Med. Chem.*, 26, 1582 (1983) and *J. Med. Chem.*, 29, 2194 (1986); R. W. Lang et al., *Helvetica Chimica Acta*, 71, 596 (1988); EP 0205292 (1986); WO 87/07607; and K. S. Atwal et al., *J. Med. Chem.*, 36, 3971 (1993).

The amino alcohol of formula III where $R^3$ is cis-hydroxy can be prepared by methods described in A. Burrell et al., *Tetrahedron Letters*, 31, 3649 (1990).

The amines of formula III where $R^3$ is hydrogen, can be prepared from a ketone of the formula

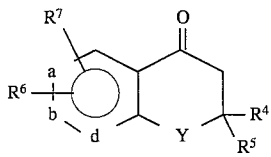    X by standard methodology.

The ketone of formula X can be obtained by literature procedures, such as described by P. Sebok et al., *Heterocycles*, 27, 2595 (1988); P. Teixidor et al., *Heterocycles*, 27, 2459 (1988); A. Benerji et al., *Tetrahedron Letters*, 3685 (1979); and A. Ariamola et al., *Tetrahedron Letters*, 29, 3487 (1988).

The amines of formula III where RS is hydrogen can also be prepared from olefins of the formula

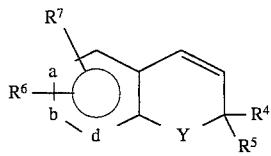    XI by a sequence of steps which involve; (a) catalytic hydrogenation of the double bond; (b) bromination of the resulting compound with N- bromosuccinimide and light; (c) displacement of the bromide with azide using sodium azide followed by; (d) catalytic reduction of the azide.

Amines of formula III wherein Y is a single bond can be prepared according to D. R. Buckle et al., *J. Med. Chem.*, 34, 919 (1991).

Amines of formula III where Y is $-CH_2-$ or $-N(R^8)-$ can be prepared by methods described in V. A. Ashwood et al., *J. Med. Chem.*, 34, 3261 (1991).

Amines of formula III wherein Y is $-C(O)-$ can be prepared by methods described in C. Almansa et al., *J. Med. Chem.*, 36, 2121 (1993).

Amines of formula III wherein Y is $-S-$ can be prepared according to D. Smith et al., EP-0322251.

Compounds of formula IV, V, VI, VII, VIII, and IX are commercially available or may be prepared from commercially available materials by standard methods described in the literature for example, Introduction to Organic Chemistry by A. Streiwieser and C. H. Heathcock, Macmillan Publishing Co., Inc., N.Y., pages 461, 495, 786, 954 and 969 (1976).

Compounds of formula X may be prepared by J. M. Evans et al., *J. Med. Chem.*, 26, 1582 (1983).

If any of the reagents or intermediates used for the preparation of compounds of formula I contain reactive functional groups (e.g., hydroxy, amino), they can be protected with standard protecting groups. The protecting groups can then be removed by standard methods.

All other compounds of formula I may be prepared by modification of the procedures discussed herein as known by those skilled in the art. The intermediates used to prepare compounds of formula I are described herein or may be derived from known compounds by those skilled in the art or are commercially available.

The compounds of the present invention can have asymmetric centers at carbons 2–4 of the bicyclic ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The antiischemic and antihypertensive effects of benzopyran based and related potassium channel openers are usually stereoselective, with the 3S,4R-enantiomer being the more active isomer. However, it has been unexpectedly found that compounds of formula I are "selective antiischemic agents" with the 3R,4S-enantiomer being the more potent isomer. The term "selective antiischemic agent" means that these compounds possess little or no vasodilator activity (i.e., these compounds have $IC_{50}$ (rat aorta) values greater than that of the known potassium channel activator, cromakalim. Therefore, in the treatment of ischemic hearts, the compounds of the instant invention are less likely to cause coronary steal, profound hypotension and coronary under-perfusion.

The preferred compounds of the present invention are those compounds of formula I where:
a, b and d are carbon atoms;
Y is a single bond or $-O-$;
$R^1$ is aryl;
$R^2$ is hydrogen, $-COR^8$ or $-COOR^8$;
$R^3$ is hydroxy;
$R^4$ and $R^5$ are methyl;
$R^6$ is $-CN$, $-NO_2$, $-CF_3$, halogen or alkyl; and
$R^7$ is hydrogen.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of the compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness), and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic add tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(3S-trans)-[2-[(6-Cyano-3,4-dihydro-3-hydroxy-2,2-dimethyl-2H-1-benzopyran-4-yl)amino]-2-oxo-1-phenylethyl]carbamic acid, 1,1-dimethylethyl ester

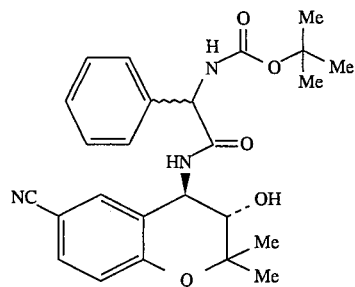

To a solution containing (D)-BOC-phenylglycine (1.0 g, 4.0 mmol) in dimethylformamide (7.0 mL) at 0° C. under argon was added 1-hydroxybenzotriazole (632 mg, 4.68 mmol) followed by dicyclohexylcarbodiimide (965 mg, 4.68 mmol). The cooling bath was removed and the reaction mixture was stirred at room temperature for one hour. To the reaction mixture were added (3-S-trans)-4-amino-3,4-dihydro-3-hydroxy-2,2-dimethyl-2H-1-benzopyran-6-carbonitrile, methanesulfonic acid salt (1.35 g, 4.25 mmol, prepared according to Atwal et al., *J. Med. Chem.*, 36, 3971 (1993)) and triethylamine (1.0 mL). It was stirred at room temperature for 16 hours and diluted with ethyl acetate. The solid was filtered off and the filtrate was washed with 10% citric acid, water, sodium bicarbonate solution and brine. After drying over anhydrous magnesium sulfate, the solvent was evaporated to yield a colorless foam (1.6 g, 88.4%) as a (~1:1) mixture of diastereomers, mp 112°–130° C. (with foaming). Analysis calculated for $C_{25}H_{29}N_3O_5$. 1.0 $H_2O$: C, 63.95; H, 6.66; N, 8.95. Found: C, 63.90; H, 6.52; N, 8.67.

EXAMPLE 2

(3S-trans)-α-Amino-N-(6-cyano-3,4-dihydro-3-hydroxy-2,2-dimethyl-2H-1-benzopyran-4-yl)benzeneacetamide (isomers A and B)

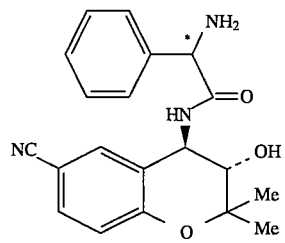

*mixture of diasteromers

To a solution containing (3S-trans)-[2-[(6-cyano-3,4-dihydro-3-hydroxy-2,2-dimethyl-2H-1-benzopyran-4-yl)amino]-2-oxo-1-phenylethyl]carbamic acid, 1,1-dimethylethyl ester (2.27 g, 5.03 mmol; the title compound of Example 1) in dichloromethane (20 mL) was added trifluoroacetic acid (5.0 mL) and the reaction mixture was stirred at room temperature for 16 hours. The volatile materials were removed under vacuum and the residue in chloroform was washed with sodium bicarbonate solution and brine. After drying over anhydrous magnesium sulfate, the solvent was evaporated and the residue was purified by flash chromatography (7.5% methanol in dichloromethane) to give two diastereomers. The faster moving material was triturated with ether to give (3S-trans)-α-amino-N-(6-cyano-3,4-dihydro-3-hydroxy-2,2-dimethyl-2H-1-benzopyran-4-yl)benzeneacetamide, isomer A (620 mg, 35.2%) as a colorless solid, mp 243°–246° C. Analysis calculated for $C_{20}H_{21}N_3O_3 \cdot 0.3H_2O$: C, 67.32; H, 6.10; N, 11.78. Found: C, 67.50; H, 5.99; N, 11.65. $[\alpha]_D = -17.2°$ (c=1, Dimethylformamide). The slower moving material was triturated with ether to give (3S-trans)-α-amino-N-(6-cyano-3,4-dihydro-3-hydroxy-2,2-dimethyl-2H-1-benzopyran-4-yl)-benzeneacetamide, isomer B (940 mg, 53.4%) as a colorless solid, mp 109°–111° C. (with foaming). Analysis calculated for $C_{20}H_{21}N_3O_3 \cdot 0.45H_2O$: C, 66.82; H, 6.14; N, 11.69. Found: C, 67.14; H, 6.32; N, 11.14. $[\alpha]D = +29.2°$ (c=1, Dimethylformamide).

EXAMPLE 3

(3S-trans)-N-[2-[(6-Cyano-3,4-dihydro-3-hydroxy-2,2-dimethyl-2H-1-benzopyran-4-yl)amino]-2-oxo-1-phenylethyl]acetamide

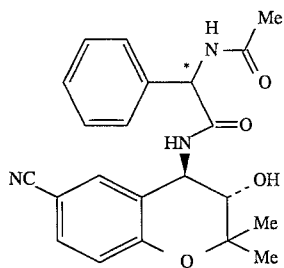

*mixture of diastereomers

To a solution containing (3S-trans)-α-amino-N-(6-cyano-3,4-dihydro-3-hydroxy-2,2-dimethyl-2H-1-benzopyran-4-yl)benzeneacetamide (340 mg, 0.97 mmol; isomer A of the title compound of Example 2) in tetrahydrofuran (10 mL, a few drops of methanol were added to obtain a clear solution) at room temperature was slowly added excess acetyl chloride while maintaining the reaction at pH ~8.5 by simultaneous addition of 7% sodium carbonate solution. After the completion of the reaction, it was diluted with ethyl acetate and washed with water and brine. After drying over anhydrous magnesium sulfate, the solvent was evaporated to provide a colorless solid (320 mg, 84.2%) which was recrystallized from hot 2-propanol to give (3S-trans)-N-[2-[(6-cyano-3,4-dihydro-3-hydroxy-2,2-dimethyl-2H-1-benzopyran-4-yl )amino]-2-oxo-1-phenylethyl]acetamide, mp 234°–236° C. Analysis calculated for $C_{22}H_{23}N_3O_4 \cdot 0.2H_2O$: C, 66.55; H, 5.94; N, 10.58. Found: C, 66.71; H, 5.58; N, 10.56. $[\alpha]_D = -91.2°$ (c =0.5, MeOH).

EXAMPLE 4

(3S-trans)-N-[2-[(6-Cyano-3,4-dihydro-3-hydroxy-2,2-dimethyl-2H-1-benzopyran-4-yl)amino]-2-oxo-1-phenylethyl]acetamide

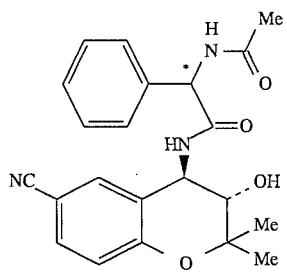

*mixture of diastereomers

To a solution containing (3S-trans)-α-amino-N-(6-cyano-3,4-dihydro-3-hydroxy-2,2-dimethyl-2H-1-benzopyran-4-yl)benzeneacetamide (600 mg, 1.7 mmol; isomer B of the title compound of Example 2)in tetrahydrofuran (7 mL) at room temperature was slowly added excess acetyl chloride while maintaining the reaction at pH ~8.5 by simultaneous addition of 7% sodium carbonate solution. After the completion of the reaction, it was diluted with ethyl acetate and washed with water and brine. After drying over anhydrous magnesium sulfate, the solvent was evaporated to provide a colorless gum (518 mg, 77.2%) which was stirred with ether to give (3S-trans)-N-[2-[(6-cyano-3,4-dihydro-3-hydroxy-2,2-dimethyl-2H-1-benzopyran-4-yl)amino]-2-oxo-1-phenylethyl]acetamide, mp 133°–145° C. (starts shrinking@124° C). Analysis calculated for $C_{22}H_{23}N_3O_4 \cdot 0.4H_2O$: C, 65.95; H, 5.99; N, 10.49. Found: C, 66.09; H, 5.92; N, 10.30. $[\alpha]_D = +62.4°$ (c=0.5, MeOH).

EXAMPLE 5

(3S*,4R*)-N-(6-Cyano-3,4-dihydro-3-hydroxy-2,2-dimethyl-2H-1-benzopyran-4-yl)-$N^2$-[(1,1-dimethylethoxy)carbonyl]-D-phenylalaninamide

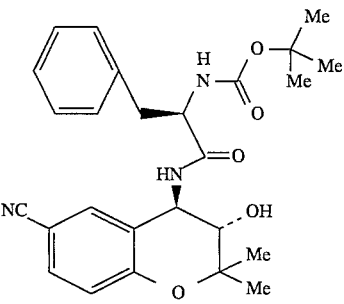

The title compound was prepared from BOC-D-phenylalanine and (3-S-trans)-4-amino-3,4-dihydro-3-hydroxy-2,2-dimethyl-2H-1-benzopyran-6-carbonitrile, methanesulfonic acid salt (1.35 g, 4.25 mmol, prepared according to Atwal et al., *J. Med. Chem.*, 36, 3971 (1993)) by the same procedure as described for the title compound of Example 1. The product was purified by flash chromatography (60% hexanes in ethyl acetate) and triturated with ethyl ether to give the title compound as a colorless solid, mp 192°–194° C. Anal. calculated for $C_{26}H_{31}N_3O_5 \cdot 0.07 \ H_2O$: C, 67.03; H, 6.52;

N,9.02. Found: C, 67.03; H, 6.97; N, 9.02. $[\alpha_D]^{25}=-21.9°$ (c=0.338, MeOH).

EXAMPLE 6

(3R*,4S*)-N-(6-Cyano-3,4-dihydro-3-hydroxy-2,2-dimethyl-2H-1-1-benzopyran-4-yl)-D-phenylalaninamide

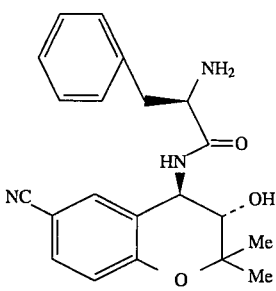

The title compound was prepared from the title compound of Example 5 by the same procedure as described for the title compound of Example 2. The residue was triturated with ethyl ether to give a colorless solid, mp 208°–211° C. Analysis calculated for $C_{21}H_{23}N_3O_5 \cdot 0.23$ $H_2O$: C, 68.26; H, 6.40; N,11.37. Found: C, 68.39; H, 6.70; N, 11.24. $[\alpha_D]^{25}=-32.1°$ (c=0.408, MeOH).

EXAMPLE 7

(3S*,R*)-N²-Acetyl-N-(6-cyano-3,4-dihydro-3-hydroxy-2,2-dimethyl-2H-1-benzopyran-4-yl)-D-phenylalaninamide

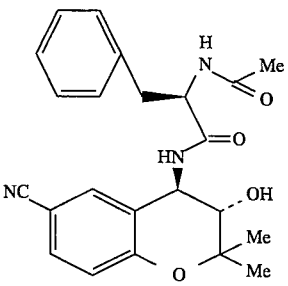

A solution of the title compound of Example 6 (0.25 g, 0.68 mmol) in dichloromethane (5 mL) under argon was treated with sodium acetate (0.60 mg, 0.73 mmol) followed by acetic anhydride (35 mg, 0.35 mmol). The reaction mixture was stirred at room temperature for 30 minutes, diluted with dichloromethane (200 mL) and washed with saturated sodium bicarbonate solution and brine. After drying over anhydrous magnesium sulfate, the solvent was evaporated in vacuo and the residue was triturated with ethyl ether to give the title compound (0.18 g, 64%) as a colorless solid, mp 181°–184° C. Analysis calculated for $C_{23}H_{25}N_3O_4$: C, 67.80; H, 6.18; N, 10.31. Found: C, 67.52; H, 6.49; N, 10.34. $[\alpha_D]^{25}=-13.0°$ (c=0.291, MeOH).

EXAMPLE 8

(3R*,4S*)-N-(6-Cyano-3,4-dihydro-3-hydroxy-2,2-dimethyl-2H-1-benzopyran-4-yl)-N²-[(1,1-dimethylethoxy)carbonyl]-L-phenylalaninamide

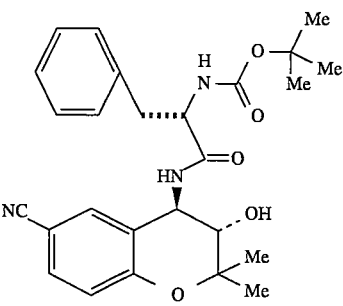

The title compound was prepared from BOC-L-phenylalanine and (3-S-trans)-4-amino-3,4-dihydro-3-hydroxy-2,2-dimethyl-2H-1-benzopyran-6-carbonitrile, methanesulfonic acid salt (1.35 g, 4.25 mmol, prepared according to Atwal et al., J. Med. Chem., 36, 3971 (1993)) by the same procedure as described for the title compound of Example 1. The product was obtained as a colorless solid, mp 110°–112° C. Analysis calculated for $C_{26}H_{31}N_3O_5 \cdot 0.28$ $H_2O$: C, 66.50; H, 6.58; N, 8.95. Found: C, 66.50; H, 6.88; N, 8.88. $[\alpha_D]^{25}=-12.6°$ (c=0.36, MeOH).

EXAMPLE 9

(3R*,4S*)-N-(6-Cyano-3,4-dihydro-3-hydroxy-2,2-dimethyl-2H-1-benzopyran-4-yl)-L-phenylalaninamide

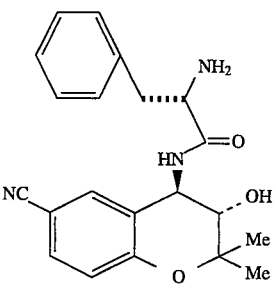

The title compound was prepared from the title compound of Example 8 by the same procedure as described for the title compound of Example 2. The product was obtained as a colorless solid, mp 125°–127° C. Analysis calculated for $C_{21}H_{23}N_3O_5 \cdot 0.39$ $H_2O$: C, 67.72; H, 6.44; N, 11.28. Found: C, 67.84; H, 6.43; N, 11.16. $[\alpha_D]^{25}=-9.1°$ (c=0.275, MeOH).

EXAMPLE 10

(3R*,4S*)-N2-Acetyl-N-(6-cyano-3,4-dihydro-3-hydroxy-2,2-dimethyl-2H-1-benzopyran-4-yl)-D-phenylalaninamide

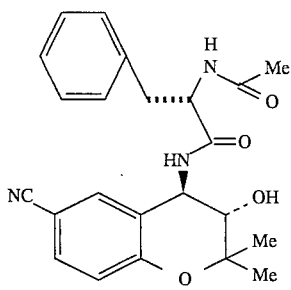

The title compound was prepared from the title compound of Example 9 by the same procedure as described for the title compound of Example 7. The product was triturated with ethyl ether to give a colorless solid, mp 181°–184° C. Analysis calculated for $C_{23}H_{25}N_3O_4 \cdot 0.17H_2O$: C, 67.29; H, 6.22; N, 10.24. Found: C, 67.22; H, 6.14; N, 10.31. $[\alpha_D]^{25} = -26.9°$ (c=0.38, MeOH).

What is claimed is:

1. A compound of the formula

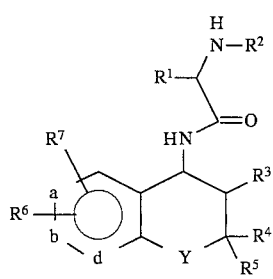

or pharmaceutically acceptable salts thereof wherein a, b and d are all carbon atoms;

Y is —O—;

$R^1$ is a aryl, (aryl)alkyl, heterocyclo or (heterocyclo)alkyl;

$R^2$ is hydrogen, alkyl, —$COR^8$, —$COOR^8$, —$CONR^8R^9$ or —$SO_2R^8$;

$R^3$ is hydrogen, hydroxy or —OC(O)$R^8$;

$R^4$ and $R^5$ are each independently hydrogen, alkyl or arylalkyl; or $R^4$ and $R^5$ taken together with the carbon atom to which they are attached form a 5- to 7-membered carbocyclic ring;

$R^6$ is hydrogen, alkyl, haloalkyl, alkenyl, alkynyl, cycloalkyl, arylalkyl, (cycloalkyl)alkyl, —CN, —$NO_2$, —$COR^8$, —$COOR^8$, —$CONHR^8$, —$CONR^8R^9$, —$CF_3$, —S-alkyl,

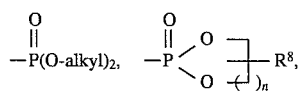

halogen, amino, substituted amino, —O-alkyl, —$OCF_3$, —$OCH_2CF_3$, —OCOalkyl, —$OCONR^8$alkyl, —$NR^8COalkyl$, —$NR^8COOalkyl$ or —$NR^8CONR^9$, tetrazolyl, imidazole, oxazole or triazole, —$SOR^8$, —$SO_2R^8$ or —$SO_2NR^8R^9$;

$R^7$ is hydrogen, alkyl, halogen, hydroxy, —O-alkyl, amino, substituted amino, —$NHCOR^8$, —CN or —$NO_2$;

$R^8$ and $R^9$ are independently hydrogen, alkyl, haloalkyl, aryl, arylalkyl, cycloalkyl or (cycloalkyl)alkyl; or $R^8$ and $R^9$ taken together with the atoms to which they are attached form a 5- to 7-membered ring; and n is an integer of 1 to 3.

2. The compound as recited in claim 1 wherein a, b and d are carbon atoms;

Y is —O—;

$R^1$ is aryl;

$R^2$ is hydrogen, —$COR^8$ or —$COOR^8$;

$R^3$ is hydroxy;

$R^4$ and $R^5$ are methyl;

$R^6$ is —CN, —$NO_2$, —$CF_3$, halogen or alkyl; and $R^7$ is hydrogen.

3. The compound as recited in claim 1, which is:

(3S-trans)-[2-[(6-cyano-3,4-dihydro-3-hydroxy-2,2-dimethyl-2H-1-benzopyran-4-yl)amino]-2-oxo-1-phenylethyl]carbamic acid, 1,1-dimethylethyl ester;

(3S-trans)-α-amino-N-(6-cyano-3,4-dihydro-3-hydroxy-2,2-dimethyl-2H-1-benzopyran-4-yl)benzeneacetamide (isomers A and B);

(3S-trans )-N-[2-[(6-cyano-3,4-dihydro-3-hydroxy-2,2-dimethyl-2H-1-benzopyran-4-yl)amino]-2-oxo-1-phenylethyl]acetamide;

(3S-trans)-N-[2-[(6-cyano-3,4-dihydro-3-hydroxy-2,2-dimethyl-2H-1-benzopyran-4-yl)amino]-2-oxo-1-phenylethyl]acetamide;

(3S*,4R*)-N-(6-cyano-3,4-dihydro-3-hydroxy-2,2-dimethyl-2H-1-benzopyran-4-yl)-N2-[(1,1-dimethylethoxy)carbonyl]-D-phenylalaninamide;

(3R*,4S*)-N-(6-cyano-3,4-dihydro-3-hydroxy-2,2-dimethyl-2H-1-benzopyran-4-yl)-D-phenylalaninamide;

(3S*,R*)-N²-acetyl-N-(6-cyano-3,4-dihydro-3-hydroxy-2,2-dimethyl-2H-1-benzopyran-4-yl )-D-phenylalaninamide;

(3R*,4S*)-N-(6-cyano-3,4-dihydro-3-hydroxy-2,2-dimethyl-2H-1-benzopyran-4-yl)-N2-[(1,1-dimethylethoxy)-carbonyl]-L-phenylalaninamide;

(3R*,4S*)-N-(6-cyano-3,4-dihydro-3-hydroxy-2,2-dimethyl-2H-1-benzopyran-4-yl )-L-phenylalaninamide;

(3R*,4S*)-N²-acetyl-N-(6-cyano-3,4-dihydro-3-hydroxy-2,2-dimethyl-2H-1-benzopyran-4-yl)-D-phenylalaninamide; or pharmaceutically acceptable salts thereof.

4. A pharmaceutical composition comprising a compound of claim 1 and a pharmaceutically acceptable carrier.

5. A method for treating ischemia comprising administering to a mammalian specie in need thereof a therapeutically effective amount of a composition of claim 4.

* * * * *